United States Patent [19]

Rodel et al.

[11] Patent Number: 5,419,211
[45] Date of Patent: May 30, 1995

[54] DEVICE FOR TAKING SOIL SAMPLES
[75] Inventors: Gerhard Rodel; Manfred Schurig, both of Freising, Germany
[73] Assignee: Georg Fritzmaier GmbH & Co., Grosshelfendorf, Germany
[21] Appl. No.: 217,142
[22] PCT Filed: Feb. 12, 1990
[86] PCT No.: PCT/EP90/00226
    § 371 Date: Aug. 9, 1991
    § 102(e) Date: Aug. 9, 1991
[87] PCT Pub. No.: WO90/09508
    PCT Pub. Date: Aug. 23, 1990

Related U.S. Application Data

[63] Continuation of Ser. No. 741,411, Aug. 9, 1991, abandoned.

[30] Foreign Application Priority Data

Feb. 11, 1989 [DE] Germany .................. 39 04 105.0
Nov. 16, 1989 [DE] Germany .................. 39 38 166.8
Jan. 11, 1990 [DE] Germany .................. 40 00 677.8

[51] Int. Cl.⁶ .................................................... G01N 1/04
[52] U.S. Cl. ............................... 73/864.45; 73/864.44
[58] Field of Search ................... 73/864.44, 864.45; 175/20-23, 58, 403; 408/204, 205

[56] References Cited

U.S. PATENT DOCUMENTS

| 64,192 | 4/1867 | Budd | 175/22 |
|---|---|---|---|
| 1,008,904 | 11/1911 | Harden et al. | 73/864.44 |
| 2,779,195 | 1/1957 | Simon | 73/864.44 |
| 3,163,456 | 12/1964 | Schell, Jr. et al. | 73/864.44 |
| 3,367,188 | 2/1968 | Robinson | 73/864.44 |
| 3,372,760 | 3/1968 | Raymond et al. | 73/864.44 |
| 3,447,615 | 6/1969 | Schick | 175/17 |
| 3,562,916 | 2/1971 | Duckworth | 73/784 |
| 3,690,389 | 9/1972 | Beld et al. | 175/59 |
| 3,817,338 | 6/1974 | Guest . | |
| 3,872,935 | 3/1975 | Mielke | 175/20 |
| 3,896,663 | 7/1975 | Ogura | 73/784 |
| 3,949,819 | 4/1976 | Tanov | 175/243 |
| 4,329,882 | 5/1982 | Kaup | 73/864.44 |
| 4,333,541 | 6/1982 | Dotty . | |
| 4,346,612 | 8/1982 | Rand | 73/864.44 |
| 4,598,777 | 7/1986 | Park et al. | 175/58 |
| 4,827,776 | 5/1989 | Gale et al. | 73/864.45 |
| 4,848,484 | 7/1989 | Clements | 73/864.44 |
| 4,860,599 | 8/1989 | Griffis | 73/864.44 |

FOREIGN PATENT DOCUMENTS

| 1177854 | 9/1964 | Germany . | |
|---|---|---|---|
| 1208527 | 7/1966 | Germany . | |
| 1222714 | 8/1966 | Germany . | |
| 2005539 | 9/1970 | Germany . | |
| 2435884 | 2/1976 | Germany . | |
| 2545851 | 4/1977 | Germany . | |
| 3709719 | 10/1988 | Germany . | |
| 3743416 | 6/1989 | Germany . | |
| 8906694 | 7/1989 | Germany . | |
| 3803159 | 8/1989 | Germany . | |
| 0026893 | 2/1977 | Japan | 73/864.44 |
| 2152100 | 7/1985 | United Kingdom . | |
| 0617518 | 7/1978 | U.S.S.R. | 175/58 |
| 0645050 | 1/1979 | U.S.S.R. | 73/864.45 |
| 1065535 | 1/1984 | U.S.S.R. | 73/784 |

OTHER PUBLICATIONS

Din 19672 B1.1, Apr., 1968, Deutsche Normen, "Bodenentnahmegerate fur den Landeskulturbau".
Din 19672 B1.2, Apr., 1968, Deutsche Normen, "Bodenentnahmegerate fur den Landeskulturbau".

Primary Examiner—Robert Raevis
Attorney, Agent, or Firm—Handal & Morofsky

[57] ABSTRACT

A device is disclosed for collecting a sample body, employable either in functional connection with a "handling" unit or as a manual boring rod. The device has a probe with a cylindrical tubular jacket at the head end of which is provided a manipulating means closing off the head end of the probe, which means may Be provided with an impact pad or a means of connection to the "handling" unit. The tubular jacket bounds a receiving space for the sample body or for a receptacle to accommodate the sample body, said receiving space opening into the passage of a tip arranged at the foot end of the tubular jacket, and a non-return means consisting of at least two spring wires protrudes into the receiving space. To reduce the force required for driving in and extracting the tip, it may be of the form of a truncated double cone, with a peripheral segment projecting radially beyond the tubular jacket.

24 Claims, 11 Drawing Sheets

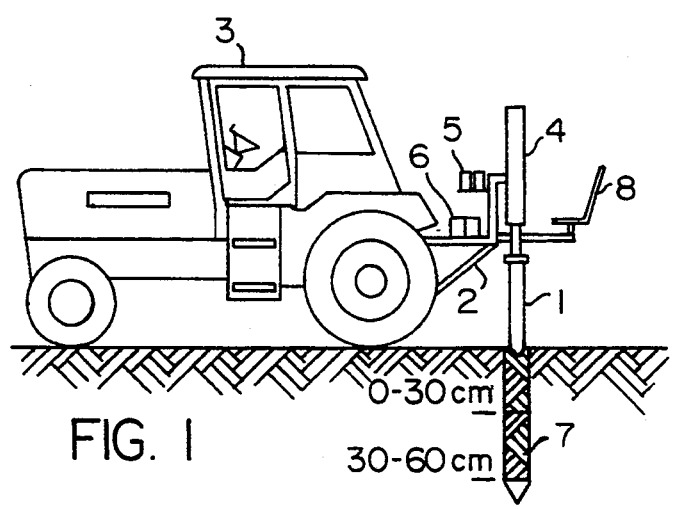
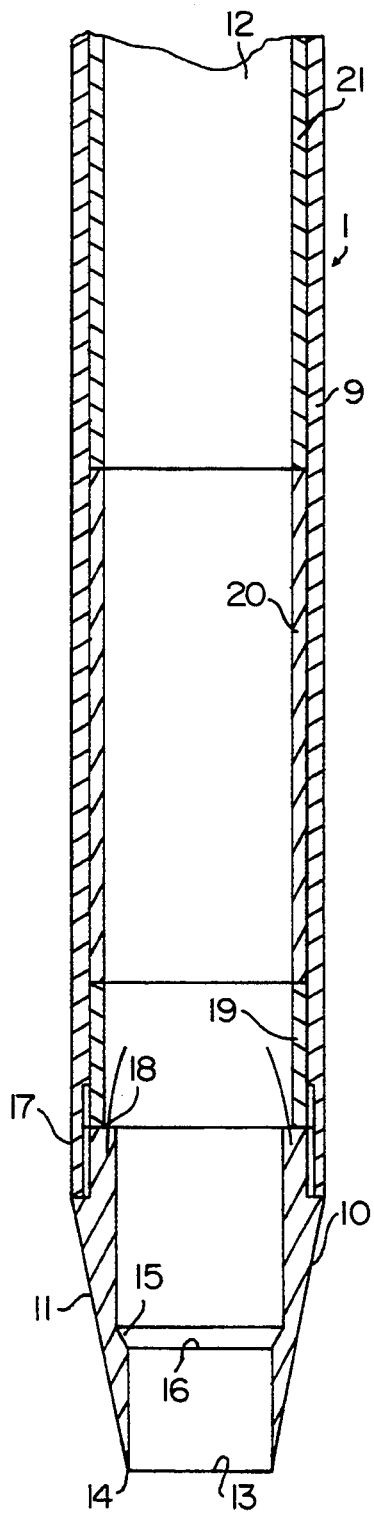
FIG. 1
FIG. 2

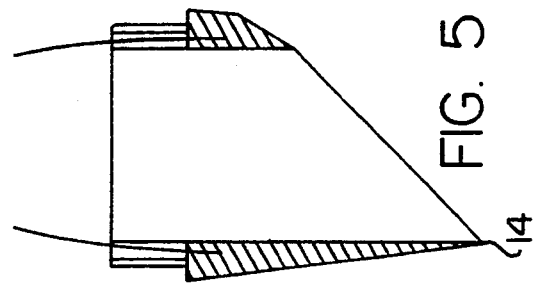
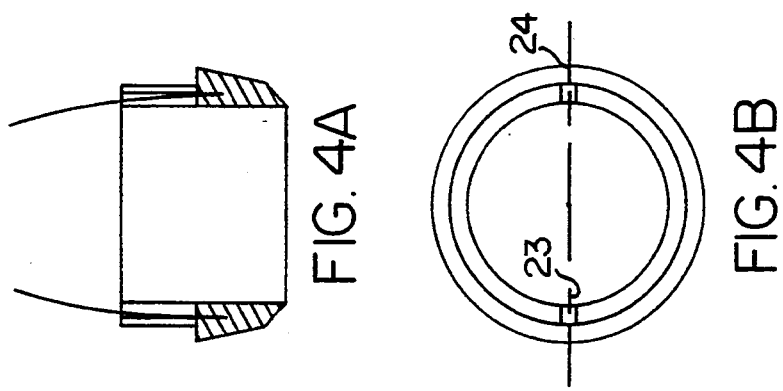
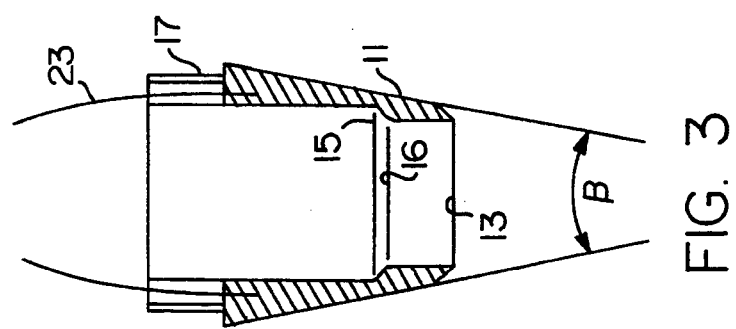

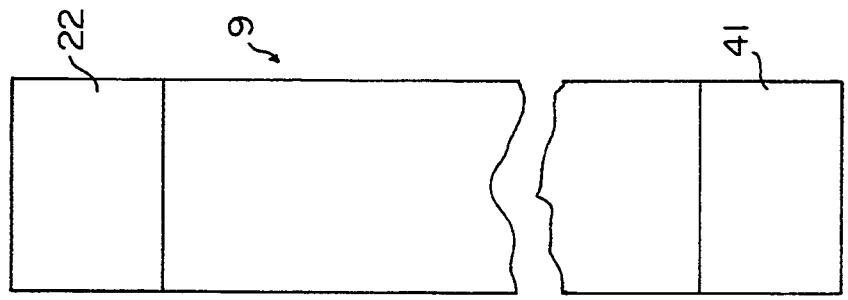
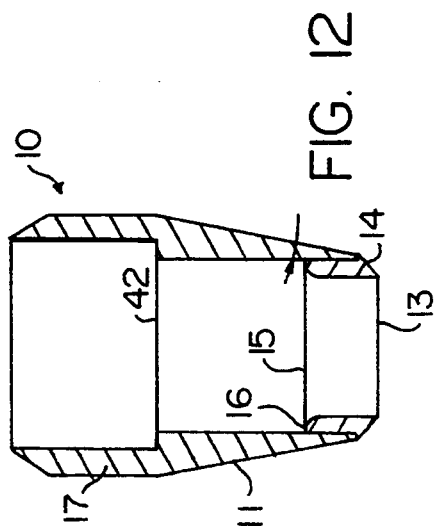
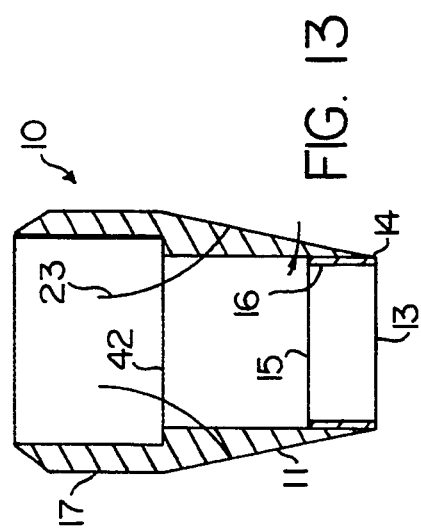

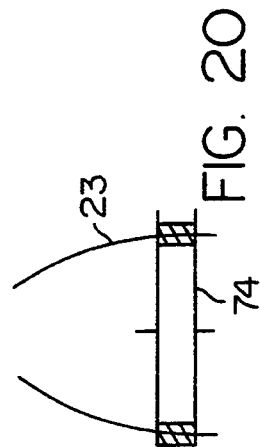
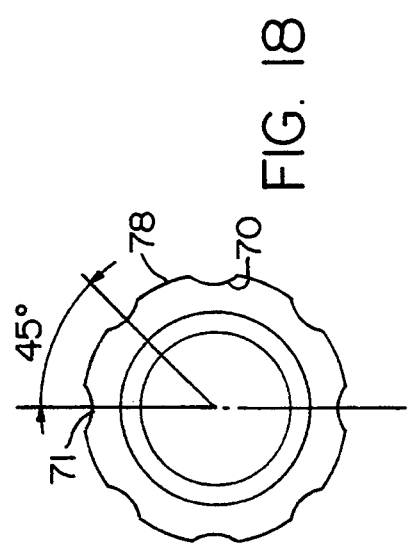
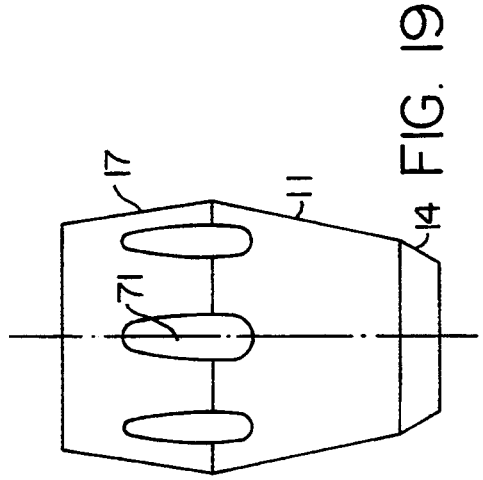

DEVICE FOR TAKING SOIL SAMPLES

This application is a continuation of application Ser. No. 07/741411, filed Aug. 9, 1991, now abandoned.

BACKGROUND OF THE INVENTION

The invention relates to a device for taking soil samples, according to the generic clause of claim 1.

Overfertilizing of the soil of areas in agricultural use and the associated pollution of waters has increasingly been a subject of public concern recently. Agricultural operations are increasingly adopting the practice of regular soil testing. By analysis for nutrients and alternation of products of cultivation, fertilizing can be optimized and soil exhaustion prevented. It can be ascertained whether the texture of the soil is intact, whether the soil is well aerated, and whether the soil contains an adequate proportion of humus.

Hitherto, samples have been taken by means of probes driven into the ground and then removed, bringing along the section of soil enclosed by the probe.

Probes employed heretofore, as known for example from German Letters of Disclosure 2,545,851, have a tubular jacket bearing a replaceable tip at its foot end segment. The receiving space formed by the tubular jacket is closable towards the tip of the probe by a closure flap, whereby the body of the sample is automatically enclosable in the probe when the probe is extracted. With the use of such probes, however, it has been found that in the case of highly viscous soils, the closure flap must be prestressed with a very heavy spring load in order to hold the body of the sample dependably inside the probe. This heavy spring load, of course, involves the danger that the soil sample may be damaged or its structure affected by the closure flap. With the use of a receptacle arranged coaxially in the tubular jacket to accommodate the body of the sample, the bearing of the closure flap must be passed through the receptacle, substantially augmenting the outlay for the engineering and fabrication of a probe.

SUMMARY OF THE INVENTION

The object of the invention is to perfect the generic soil sampling device so that, while reducing the mechanical outlay, a rapid sampling free from mixture is ensured.

By virtue of the spring wires projecting inward into the receiving space, the soil sample is dependably retained inside the probe when extracted, without alteration in the structure of the sample. According to the invention, the tubular jacket itself may be used as a receptacle to hold the body of the sample, the tip and the manipulating means being removed and the jacket closed by means of suitable closure caps.

In use of the device according to the invention in conjunction with a "handling" device, it is advantageous, in terms of simple construction, if the tip makes a flush connection with the tube jacket while advantageously, a receptacle to receive the body of the sample is provided in the interior of the tubular jacket.

In the case of manual boring rods a stable connection between tip and tubular jacket, and a double-cone-shaped construction of the jacket of the tip facilitates extraction of the probe from the soil.

By setting the cutting edge at various angles to the centerline of the probe, the tip of the probe can he adapted to different states of the soil, Venting the volume portion of the sample hole located below the tip of the probe by way of a recess made in the probe, the formation of a vacuum when the probe is extracted is prevented, and the forces required for extraction therefore substantially reduced. Such recesses are simple to clean, so that they are effective even for soils with high adhesion to the probe material.

The body of the sample is protected from consolidation or compression by interactions with the neighboring peripheral surfaces of the tubular jacket.

The non-return means is attached in the passage through the tip, and serves in turn for axial support of the tubular jacket. By this measure, the probe can he adapted in simple manner to different states of the soil by interchanging the non-return means.

Advantageously, two receptacles are arranged immediately adjacent to each other in the probe in the form of sleeves of predetermined length. By virtue of this refinement, by driving the probe in once, two samples can be taken from different soil strata, thus ascertaining soil properties as functions of stratum.

An especially simple construction of the probe appears when at the upper end thereof an articulating cuff is arranged, which in turn is releasably articulated to a manipulating means closing the probe in unswung condition and at the same time serving as abutment for the sleeves, extraction of the sleeves being substantially facilitated.

An impact attachment acts by way of a collar on the tubular jacket, thus averting damage to the jacket by direct impact. By replacing the collar and the tip with closing parts, the tubular jacket can be put to use as a receptacle for holding the body of the sample. For further sampling, the collar and the tip are screwed onto an unused tubular jacket.

With a view to ongoing soil monitoring, if the probe as part of a special transportable unit is driven into the soil mechanically by for example continuous pressure, and such a special unit is for example embodied as an attachment to a land vehicle, in particular a tractor, to afford utmost mobility with immediate readiness for service.

For proper laboratory preparation of samples in the field or for immediate examination of the samples, it is advantageous to provide a comminution means whereby the sets of samples can be milled and homogenized in composition.

An embodiment forms a manual boring rod of especially simple construction, capable of being driven into and extracted from the soil with substantially less resistance than known manual boring rods.

An employment of probes with a tip provides sampling with minimal application of force, the body of the sample being reliably retained inside the probe when the probe is extracted from the ground by use of a non-return means.

BRIEF DESCRIPTION OF THE DRAWING

The invention will be illustrated in more detail below in terms of several embodiments by way of example, with reference to schematic drawings. In the drawings, FIG. 1 shows a general view of a sampling unit mounted on a tractor, FIG. 2 shows a sectional view of the foot end of an embodiment of a probe by way of example, FIGS. 3, 4A, 4B, and 5 show partial sections of preferred embodiments of the tip of the probe by way of example.

FIG. 14 shows a tubular jacket of the embodiment of FIG. 11 by way of example,

FIG. 18 shows a top view of the tip of the manual boring rod of FIG. 17, FIG. 19 shows a side view of the tip of the manual boring rod of FIG. 18, and FIG. 20 shows a non-return means according to the invention, having an annular member.

DETAILED DESCRIPTION OF THE PREFERRED EMBODIMENTS

Figure 6:
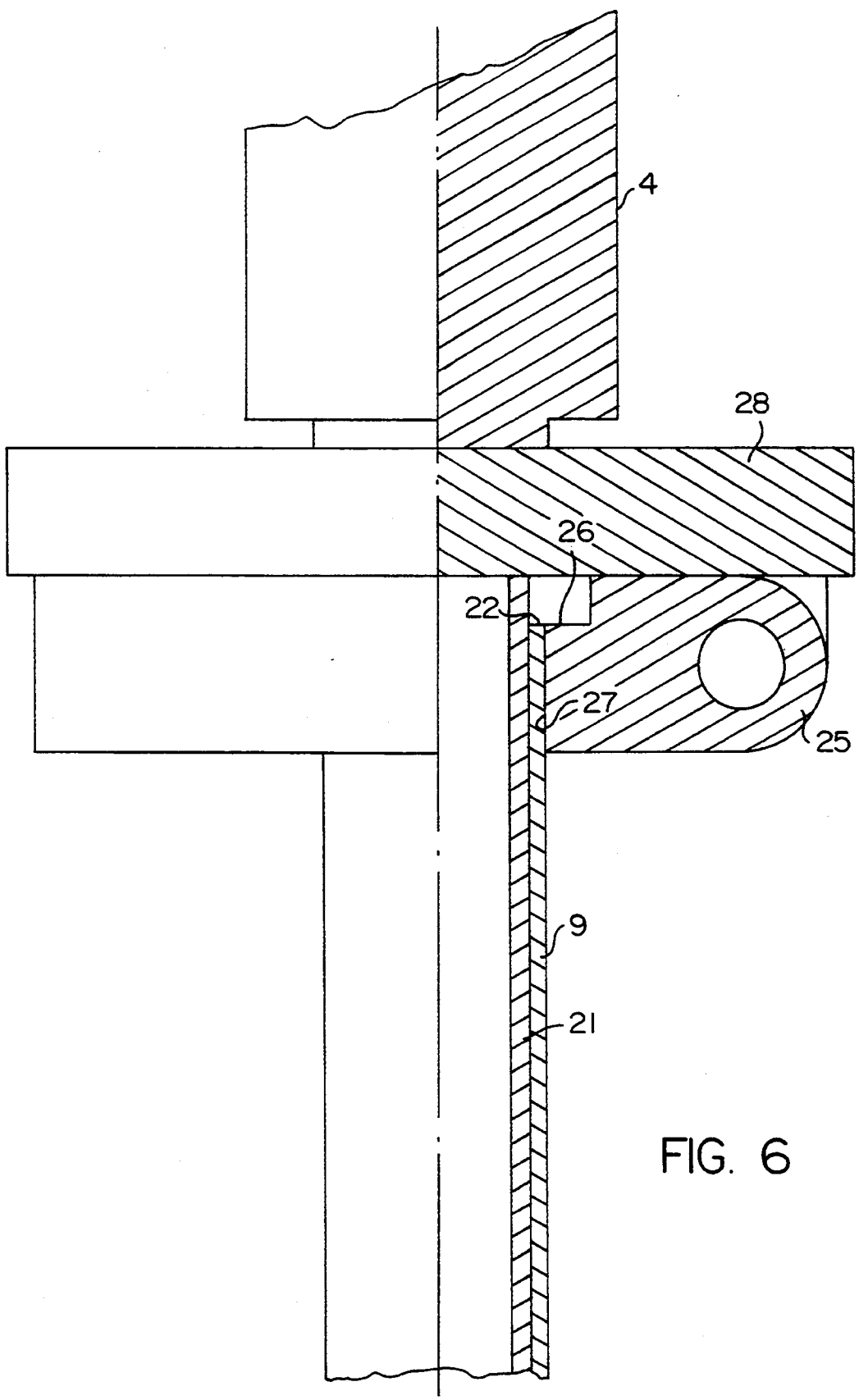
FIG. 6 shows a sectional view of the upper end of the probe of FIG. 2.

For reliable evaluation of areas for agricultural use, it is necessary to investigate the state of the soil by taking a large number of soil samples. In order that a maximum number of samples may be taken in a short time with constant sampling parameters, it is advantageous to employ the largely automated soil sampling unit as in FIG. 1, the basic principle described in the following being also applicable to other materials, as for example ensilage or the like.

In a preferred embodiment of the invention by way of example, a probe 1 for taking samples is attached to a frame 2 mounted on a land vehicle, for example a tractor 3. The frame 2 bears a double-action hydraulic cylinder 4 having its own hydraulic system and power supply (here not shown) independent of the vehicle, which cylinder is functionally connected to the probe 1, and by its means the probe 1 can be driven into the soil to a desired depth and extracted again. On the frame 2, in the region of the probe 1, two sample containers 5 are provided for samples from two different depth strata. The sample containers are for example plastic bags serving to accommodate one sample set each, each set consisting of sample bodies 7 from a predetermined soil layer (e.g. 0-30 cm, 30-60 cm). Each sample container 5 is associated with a group container 6 for holding several sample sets, For reliable exclusion of environmental influences, the group containers 6 are preferably cooling containers, in which the sample bodies 7 can be kept at a constant temperature, for example 2°-3° C., In the region of the probe 1, a seat 8 is attached, from which an operator can tend the sampling device, The probe 1 has a cylindrical tubular jacket 9. (see FIG. 2), the foot end of which is so screwed to a tip 10 that its outer peripheral surface immediately adjoins the cylindrical surface of the tubular jacket 9. A substantially cylindrical passage 12 to accommodate the body 7 of a sample traverses the probe 1 in axial direction. To minimize wear and any falsification of the samples by corrosion of the probe or the like, both the tip and the tubular jacket 9 consist preferably of stainless steel. The head 11 of the tip 10 has an outer surface in the shape of a truncated cone having a vertex angle B of for example 24°, forming a cutting edge 14 with the wall of the passage 12 at its opening cross-section 13. The opening cross-section 13 in this embodiment by way of example passes perpendicular to the centerline of the probe. To prevent compression of the sample body by friction with the periphery of the passage, the passage 12 is enlarged by a radial shoulder 15 at a predetermined distance from the opening cross-section 13. To equalize the flow of the sample body inside the probe, the peripheral edge 16 of the radial shoulder 15 that is arranged closer to the probe centerline is rounded, preferably to a radius of 2 ram, An assembly segment 17 at the end of the tip 10 opposed to the opening cross-section 13 consists of a cylindrical attachment set hack radially from the adjoining peripheral edge of the outer surface of the tip 10. This attachment bears an external thread in engagement with an internal thread of the tubular jacket 9, a segment 18 of the end cross-section projecting into the interior of the passage 12 in screwed-in condition. On this segment 18, a spacer sleeve 19 rests, whose inner periphery adjoins the passage 12 in the tip 10. The spacer sleeve 19 in turn provides an axial rest for a bottom sleeve 20, on which again an upper sleeve 21 rests. By virtue of the stacked sleeves 20, 21, soil samples may be taken from two superimposed soil layers in one penetration of the probe. The two sleeves 20, 21 can be pushed in from the top open end 22 of the probe 1. By means of the spacer sleeve 19, the inside length of the probe 1 can be adapted to different sleeve lengths. Spring wire means 23 within cylindrical passage 12 assists in retaining the soil sample within the passage 12.

Depending on the composition and viscosity of the soil to be tested, different tips 10, according to FIGS. 3 to 5, can be screwed into the tubular jacket 9. In the testing of sandy soils, for example, it is advantageous to set the opening cross-section 13 at an angle of about 45° to the probe centerline (FIG. 5) and shape the passage 12 in the tip 10 with no radial shoulder 15, For materials of low viscosity or watery soils, it suffices to employ a tip 1 having a short head 11 (see FIG. 4A and 4B), since but little force is required to drive in the probe. In this example also, no radial shoulder 15 is provided. For more stable configurations of the cutting edge 14, the head 11 as in FIGS. 3 and 4A and 4B may be chamfered at 24 around the opening cross-section 13 at an angle of preferably 45°.

In the case of low-viscosity samples, advantageously a rubber cuff is used as non-return means 23.

At the upper end 22 of the tubular jacket 9 in FIG. 6, an articulated cuff 25 is attached, the open end cross-section of the tubular jacket 9 being enclosed by a hole 27 in the cuff 25 and terminating flush at the bottom surface of a recess 26 in the cuff 25. The cuff 25 is releasably articulated to a manipulating means 28, the manipulating means 28 being the end of the piston of the hydraulic cylinder 4 and closing the probe 1 in swung condition. The lengths of the two sleeves 20, 21 and the spacer sleeves 19 are so proportioned that the end cross-section of the top sleeve 21 is in contact with the manipulating means 28 when the probe is closed, so that the sleeves 19, 20, 21 are axially fixed in the probe. The outside diameter of the top and bottom sleeves 20, 21 is fitted with Slight clearance to the inside diameter of the tubular jacket 9, For simpler placement and removal of the sleeves 20, 21, the peripheral surface of the recess 26 Is at a radial distance from the peripheral surface of the bore 27, so that an upper segment of the upper sleeve 21 is accessible when the probe 1 is swung out. The articulated cuff 25 in unswung condition may be connected to an arresting means (not shown), for example a pawl or a safety pin, locking it to the manipulating means 28.

Figure 7:
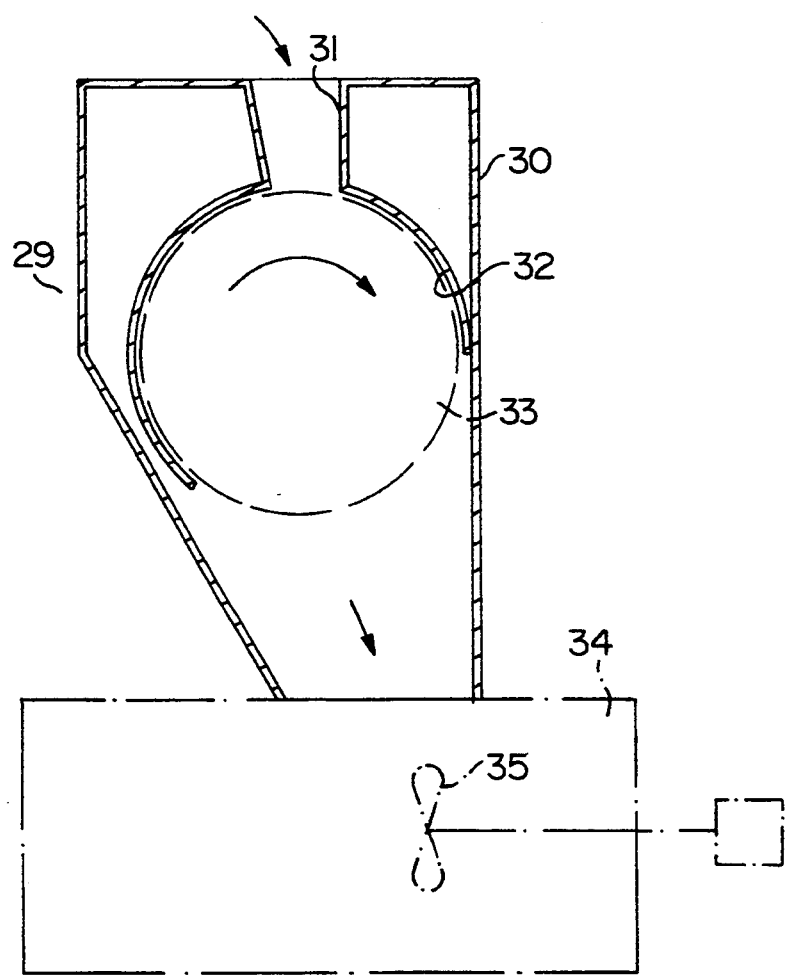
FIG. 7 shows a sectional view of a comminution and mixing means.

For preparation of the sample body 7 at the sampling location, a comminuting and mixing means 29 (see FIG. 7) may he provided on the frame 2. This consists for example of a housing 30 having in its upper portion a preferably funnel-shaped supply opening 31 leading to a comminution chamber 32. In the latter, a comminuting element 33, preferably a disc-shaped wire brush, is rotatably mounted, the drive means Being connected to the independent power supply of the frame 2. The wall of the housing of the comminution chamber 32 is at least in places at a slight distance from the peripheral and lateral surfaces of the comminuting element 33, The comminution chamber may open into a mixing container 34 having a powered mixing element 35.

In the following, the mode of operation of the subject matter of the application will be described in principle with reference to the embodiment of FIG. 1 for example.

To determine certain soil properties, sample collecting procedures have been developed. Thus for determination of nitrogen, for example, the following points must be observed:

a) A sample set consists of 15 sample bodies, i.e. 15 soil penetrations
b) The samples must be taken from the soil according to a certain pattern
c) At each penetration, two depth layers are sampled
d) The sample sets from each layer must be collected in a separate container
e) The filled containers in turn must be kept at 2°-3° C. pending laboratory processing With the subject matter of application in the embodiment according to FIGS. 1 to 7, all the steps listed under points a) to e) can be carried out in the field with great rapidity, the sampling device being carried by a land vehicle, for example a tractor. The device can be tended by one operator from the seat 8. First the tip 1 appropriate to the soil is screwed into the tubular jacket. The probe I is at this time swung 90° from the manipulating means 28, so that the upper end 22 of the probe 1 is open. In this opening, successively two sleeves 20, 21 each 30 cm in length are pushed in, the bottom sleeve 21 resting on the spacer sleeve 19. The probe is then swung back, so that the manipulating means 28 closes the probe 1 and the sleeves 20, 21 are axially fixed, The probe is driven into the ground by means of the hydraulic cylinder 4. The soil core covered by the passage 12 is thereby progressively pressed into the interior of the sleeves 20, 21. Since the passage 12 enlarges at the radial shoulder 15 in the direction of relative motion of the soil core, after passing the radial shoulder it can expand radially, the flow of the soil core being advantageously influenced by the rounding of the peripheral edge 16 of the radial shoulder 15. By these means, a consolidation of the soil core inside the probe and a compression of the sample can be reliably prevented. After the desired depth of penetration (here about 60 cm) has been reached, the probe is withdrawn from the ground by the hydraulic cylinder 4, When the probe 1 is driven in, the spring wires of the retention lock 23 are bent by the entering soil core towards the periphery of the passage 12. Upon lifting the probe 1, the soil core slides in the sleeves 20, 21, initially towards the opening cross-section 13 of the probe 1. This spreads the springs 23 so that they prevent further slippage of the soil core in the sleeves 20, 21, separating it from the earth. To collect the sample body 2, the probe 1 is swung by means of the articulated cuff 25 relative to the hydraulic arm 4. Then the two sleeves 20, 21 filled with soil can be removed. Since they are arranged immediately one above the other in the probe 1 and each has a length of 30 cm, the device according to the invention yields two samples from different soil strata in one operation, which are neither mingled nor compressed, nor in any other way altered in their original properties by the sampling operation, The sleeves 20, 21 may now be closed and passed on to a laboratory for individual examination, or, according to the above specification, each is collected in a sample container 5 associated with a particular depth layer. The tractor then moves on to the next point of penetration called for by the program, and sampling is recommended, The process described above is repeated until a set of samples is complete, Then the sample containers 5 containing a set of samples are marked and packed in a group container 6 representing a soil stratum, pending further processing.

For proper laboratory preparation of the sample in the field and to reduce transport volume, a sample set may for example be comminuted and homogeneously mixed in the comminution means 29 and mixer 34, 35 attached to the frame 2, thus yielding a sample for field analysis or laboratory study, for example nitrogen determination. In this way a series of preparatory procedures and analyses formerly carried out in the laboratory can now be performed at the place of sampling.

Figure 9:
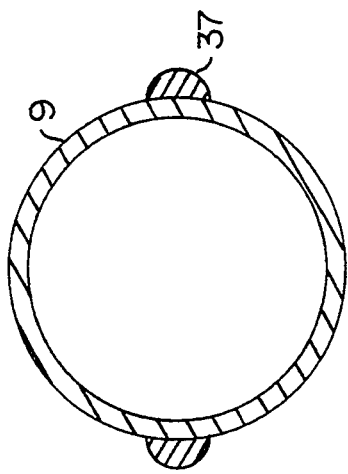
FIG. 9 shows an advantageous modification of the embodiment of FIG. 8 by way of example.
Figure 8:
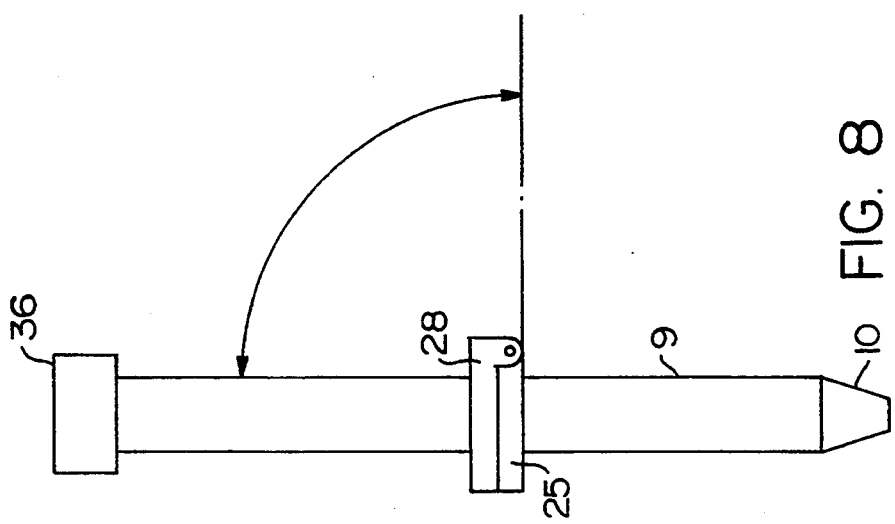
FIG. 8 shows a view of another embodiment of the probe for use as a manual boring rod.

FIGS. 8 and 9 show a simplified example of an embodiment of a soil sampling device to be used as a socalled manual boring rod when it is feasible to drive the probe in by hand, for example with blows of a hammer, and only occasional samples are to be taken, The construction of the probe 1 with articulated cuff 25 and attached manipulating means 28 is the same as in the embodiments previously described by way of example. On the manipulating means 28, in prolongation of the probe 1, an impact pad 36 is provided, whereby the probe can be hammered into the earth. Preferably the bulges 37 arranged on the outer periphery of the tubular jacket 9 in axial direction, for example approximately semicircular in cross section, are placed diametrally opposed to each other. These bulges 37 present no appreciable resistance when the probe 1 is driven in. To extract the probe 1, the impact pad 36 can he swung about 90° on the pivot of the articulated cuff. With the lever so formed, the probe can be rotated in the soil on its lengthwise axis. Then the earth adjoining the outer periphery of the probe 1 is displaced by the bulges 37 and the periphery of the probe is cut free. The probe may then be easily withdrawn from the soil, even manually.

Figure 10:
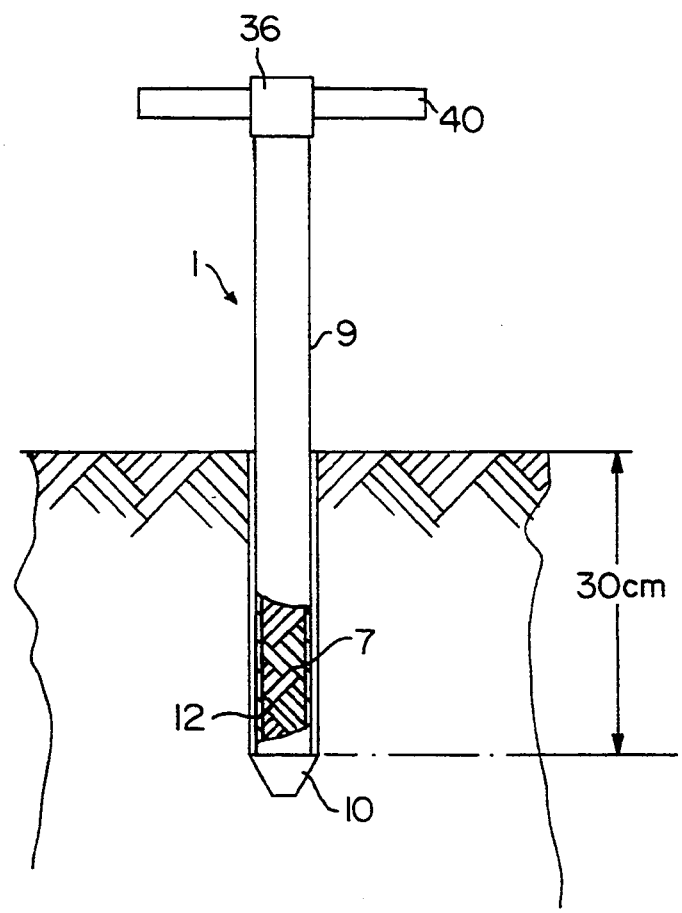
FIG. 10 shows a schematic representation of another embodiment of a manual boring rod by way of example.
Figure 11:
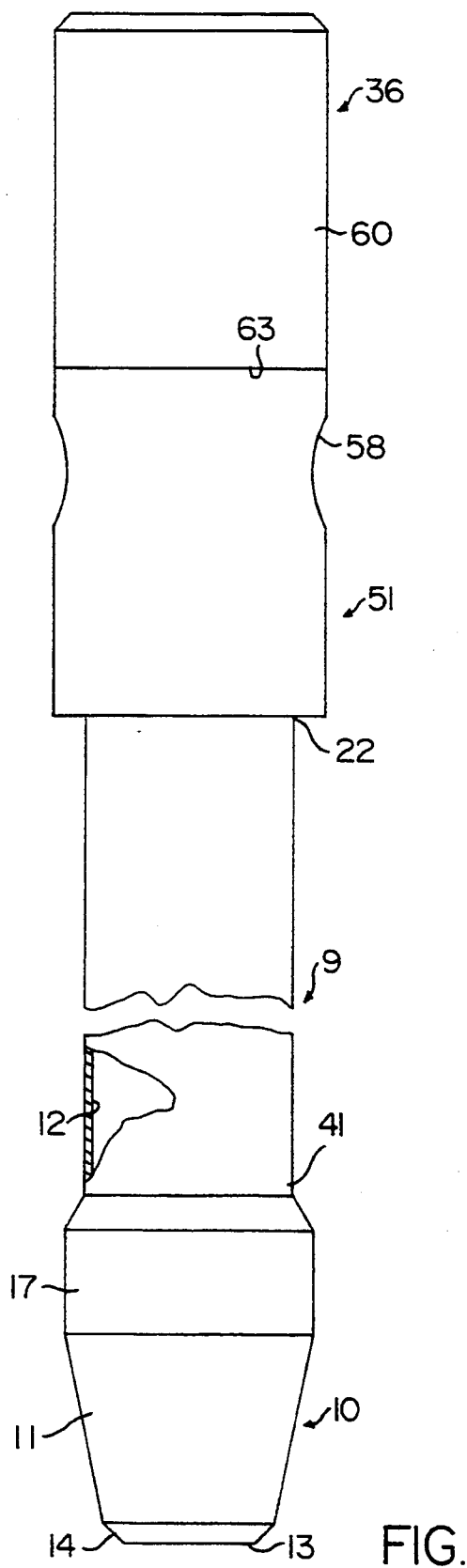
FIG. 11 shows an assembly drawing of the embodiment of a manual boring rod in FIG. 10, FIGS. 12 and 13 show embodiments of tips of the soil sampling device according to the invention.

FIGS. 10 and 11 shows another preferred embodiment of the invention by way of example, the probe 1 having the form of a manual boring rod as in FIGS. 8, 9.

The manual boring rod of FIG. 10 has a tubular jacket 9 passing over into a radially projecting tip 10 into which the jacket 9 is screwed, The tip 10 and the tubular jacket 9 are traversed by a passage 12 opening into a cross-section 13 at the opening of the tip 10. To the upper end of the boring rod 1, an impact pad 36 is fixed, This is traversed by a cross-bar 40 whereby the boring rod 1 can be rotated on its lengthwise axis to facilitate extraction from the earth.

The tubular jacket 9 fitted with the tip 10 is driven into the soil by one person, for example with blows of a hammer, to a desired depth of 30 cm. Thus the soil core covered by the passage 12, i.e. the sample body 7, pushes progressively into the interior of the jacket 9. After the desired sample depth has been reached the boring rod 1 is rotated about its lengthwise axis by means of the cross-bar 40 and extracted from the sampling hole.

The tip 10 and impact pad 36 may then be removed from the tubular jacket 9 accommodating the soil body 7 and the jacket closed with caps (not shown), so that the tubular jacket 9, by contrast with the preceding embodiments, may itself serve as receptacle for the sample body 7 to be transported for further processing or laboratory analysis.

The foot end 41 of the tubular jacket 9 is screwed by an external thread into an assembly segment 17 of the tip 10, so that the assembly segment 17 embraces the foot segment of the tubular jacket 9, projecting radially beyond its outer periphery, At the transition between the jacket 9 and the assembly segment 17, its periphery is tapered down towards the head end of the boring rod 1, so that the periphery of the assembly segment 17 gradually passes over into the tubular jacket 9, The cylindrical passage 12 traverses the manual boring rod 1 in axial direction. To minimize wear and any falsification of the samples by corrosion of the probe or the like, both the tip 10 and the tubular jacket 9 consist preferably of stainless steel. The head of the tip 10 has a periphery in the shape of a truncated cone with a vertex angle of for example 24°, forming a cutting edge 14 with the wall of the passage 12 at its opening cross section 13. In this embodiment by way of example, the opening cross-section 13 is perpendicular to the centerline of the probe.

To prevent compression of the sample body 7 by friction with the periphery of the passage 12, the latter - as may be seen in FIGS. 12 and 13 - is enlarged by a radial shoulder 15 at a predetermined distance from the opening cross-section 13. To equalize the flow of the sample body 7 inside the probe, the peripheral edge 16 of the radial shoulder 15 that is arranged nearer the centerline of the probe is rounded, preferably with a radius of 2 mm for example, According to FIGS. 12 and 13, depending on the state of the soil, various cutting breadths and transition radii may be provided.

The passage 12 (see FIGS. 12 and 13) is again enlarged in the region of the assembly segment 17 by an abutment shoulder 42 relative to the opening cross-section 13 and the radial shoulder 15, and provided with an internal thread. In screwed-in condition, the foot end 41 of the tubular jacket 9 is in contact with the abutment shoulder 42 of the assembly segment 17.

To keep the sample body 7 from slipping out of the manual boring rod 1 when lifted, a non-return means 23 protruding into the passage 12 may be provided in the tip 10 (see FIG. 13). Preferably this consists, in the case of high-viscosity samples, of two arched spring wires anchored in the shell of the tip 10. Alternatively, however, the non-return means 23 may be anchored in the shell of the tubular jacket 9.

Figure 15:
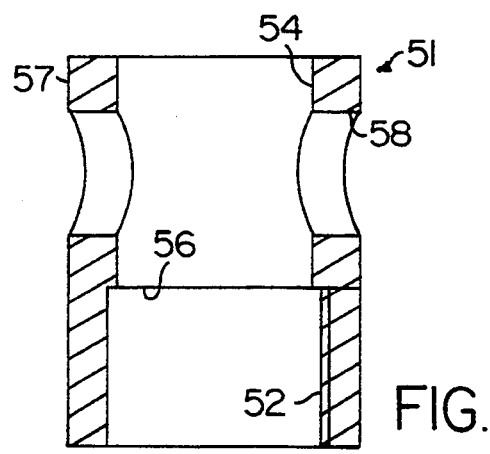
FIG. 15 shows a collar of the embodiment of FIG. 11.

At the head end 22 of the tubular jacket 9, a collar 51 (see FIGS. 11 and 15) is go fixed that the tube bore 54 of the collar 51 adjoins the passage 12, an internally threaded segment 52 being in engagement with the external thread at the head end 22 of the tubular jacket 9. The head end segment 22 of the latter is in contact with a shoulder 56 in the through bore 54, The segment 57 of the collar 51 distant from the tubular jacket 9 is traversed by a transverse hole 58 across the lengthwise axis of the boring rod 1.

Figure 16:
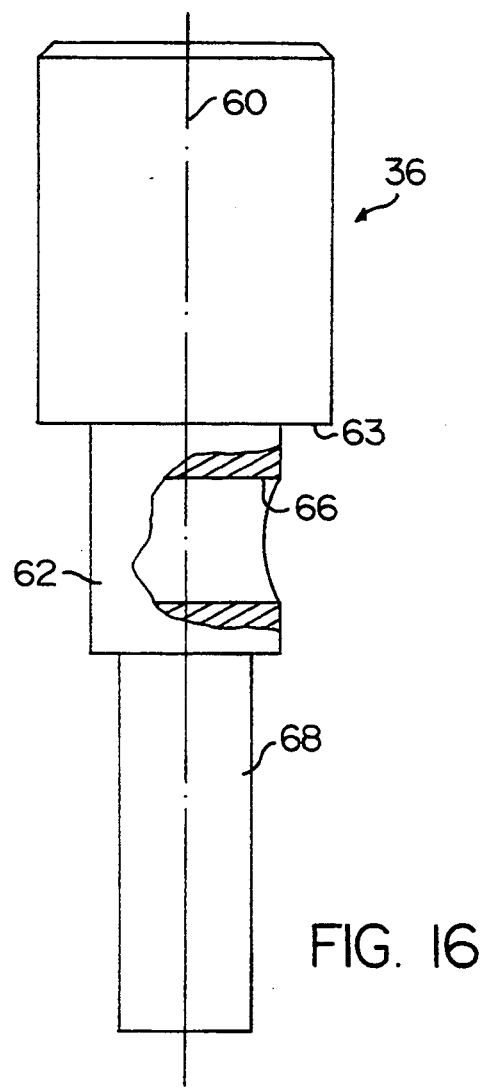
FIG. 16 shows an impact fitting for the embodiment of FIG. 11.

As may be seen in FIGS. 11 and 16, the impact pad 36 has a cylindrical head 60 radially enlarged relative to the outer periphery of the tubular jacket 9. The impact head 60 is adjoined in the direction of the tip 10 by a peg 62 rotatably guided in the segment 57 of the collar 51. The impact pad 36 in installed condition rests by a bearing segment 63 of the impact head 60 on the segment 57 of the collar 51, a radial bore 66 in the peg being alignable with the transverse bore 58, The cross-bar 40 is guided in the radial bore 66 and the transverse bore 58, and thus serves as a locking connection member between the collar 51 and the impact pad 36. The peg 63 is adjoined by a radially set-back guide segment 68, arranged coaxially at a distance from the periphery of the through bore 54, or passage 12. This guide segment 68 may for example he used as an aid to unmolding the sample body 7, for example with the impact pad removed, being introduced into the passage 12 from the opening cross-section 13 of the tip 10 and the sample body 7 being thus displaceable in the passage 12 to the head end of the boring rod 1.

The forces involved in driving in the manual boring rod 1 are uniformly distributed over the periphery by the impact pad 36 and collar 51 and transmitted to the tubular jacket 9, so that its wall thickness may be reduced to a minimum.

The tubular jacket 9, as already described, may be used as a receptacle for transport of the sample body, so that relative to the manual drilling rod of FIGS. 8, 9, a substantial weight reduction can be realized, since no separate receptacle need be carried in the boring rod 1 for keeping the sample body 7.

Figure 17:
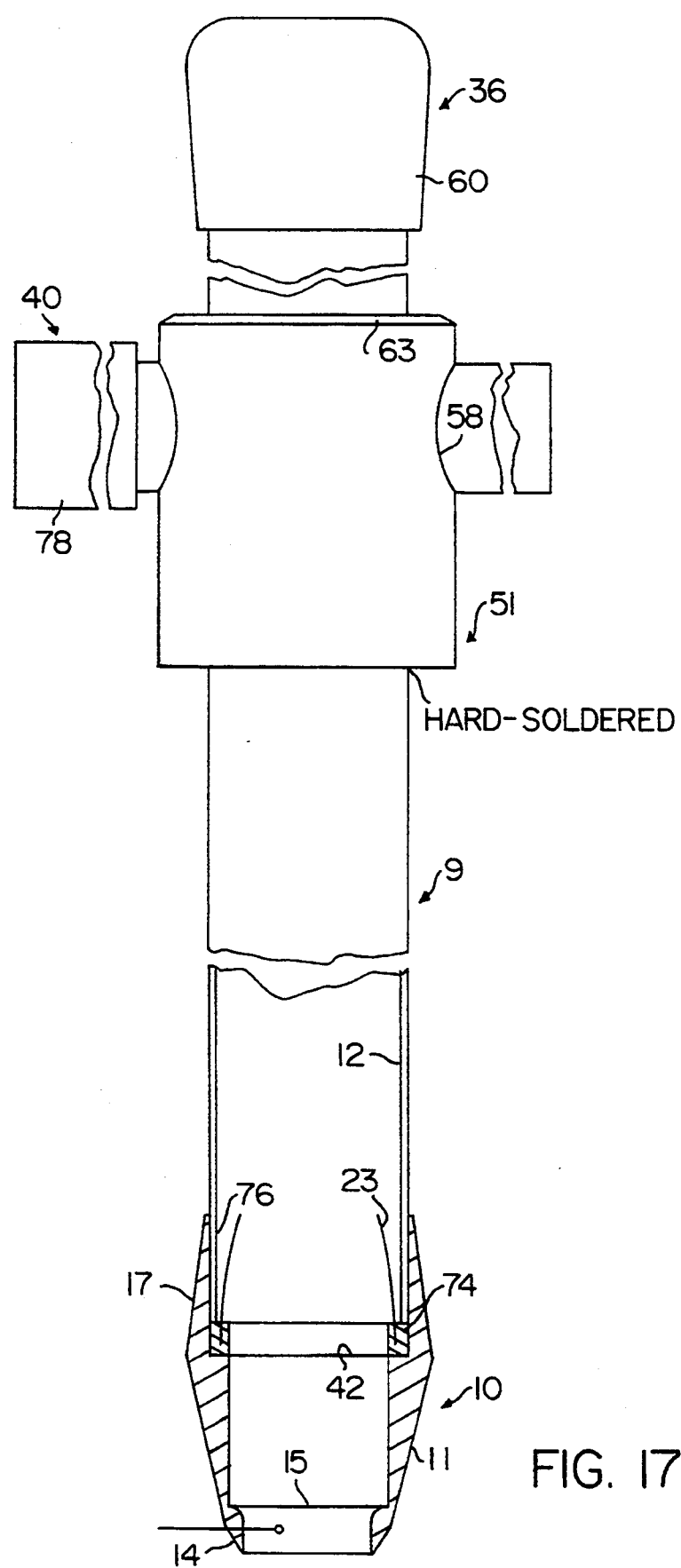
FIG. 17 shows an assembly drawing of another embodiment of a manual boring rod by way of example.

FIG. 17 shows another preferred embodiment of a manual boring rod according to the invention. In FIGS. 17 to 20, parts identical to the manual boring rod of FIGS. 8, 9–17 are designated by the same reference numerals, so that these parts need not he again described.

The manual boring rod 1 of FIGS. 17 to 20 differs from the embodiments previously described particularly in the conformation of the tip 10. In the biconical region of transition between the head 11 and the assembly segment 17, this has eight equally spaced grooves 70 distributed on the circumference, with an essentially circular cross-section. The crest lines 71 of the grooves 70 run parallel to the probe centerline and lie radially outside of the periphery of the tubular jacket 9. By virtue of the biconical configuration of the head 11 and the assembly segment 17 and the slight depth of the grooves 70, the latter run out into the periphery of the head 11 and assembly segment 17. The grooves may for example be worked into the tip 10 of FIGS. 12 and 13 by a milling operation, The configuration of the grooves 70 is of course not limited to the embodiments shown in FIGS. 18 and 19 only; rather, the grooves may instead be made of some other suitable cross-sectional shape (for example substantially rectangular, triangular, elliptical), and/or be set at an angle to the probe centerline.

The spring wires 23 forming the non-return means are fixed to an annular member 74 according to FIG. 10 in the embodiment in question. The annular member rests by its face axially distant from the spring wires 23 on the abutment shoulder 42 of the tip 10, the outer periphery of the annular member 74 being radially guided in the threaded segment 76 of the assembly segment 17, and its inner periphery terminating substantially flush with the passage 12 in the tip 10. The spring wires 23, extending essentially in axial direction, are fixed to a radially internal portion of the annular member 74 and curved arch-like towards the probe centerline. The foot end 41 of the tubular jacket 9 in screwed-in condition abuts on the face of the annular member 74 bearing the spring wires 23, the spring wires 23 opening radially within the shell of the tubular jacket 9 from the face of the annular member 74. The latter is thus fixed in axial direction by the tubular jacket 9 and the abutment shoulder 42.

As may be seen in FIG. 17, the collar 51 may alternatively be fixed to the tubular jacket 9 by a fusion process, such as for example hard soldering. The cross-bar 40 passing through the collar 51 and the impact pad 36 may have a cylindrical enlargement 78 in an end segment to serve as handle or - if the cross-bar 36 is used as a one-arm lever - as an abutment against the neighboring segment of the collar 51.

When a manual boring rod according to FIGS. 17, 18 is driven in, the grooves 70 cause protrusions of earth projecting radially inward in the periphery of the resulting sample hole, After the desired sample depth has been reached, the boring rod is rotated about the probe centerline by means of the cross-bar 36, so that the grooves 70 lie between the protrusions, Thus the portion of the protrusions located between the grooves 70 at this time is forced radially outward by the neighboring shell segments 78 of the probe, so that the earth is forced out of the grooves 70 and distributed along the neighboring peripheral segments of the sample hole. When the probe rotated relative to its position when driven in is extracted, air can escape from the annular gap between the tubular jacket and the hole through the grooves 70 into the volume portion of the sample hole located below the tip 10, thus venting that region. In this way, formation of a vacuum under the tip of the probe is reliably prevented, so that less force is required to extract the boring rod. This configuration of the boring rod 1 is especially effective for soils of high viscosity - as for example loam - since the outer periphery of the tip 10 can be in gastight contact with the periphery of the sample hole in such soils.

In the case that - for example in very hard soils - the earth occupying the grooves 70 is not displaced in rotation but sheared off, the effect of the grooves 70 is nevertheless maintained, since the earth sheared off can escape from the grooves downward when the manual boring rod 1 is extracted.

Since the grooves 70 are formed on the radially external portion of the tip with comparatively small depth, upon rotation and extraction of the probe there is only a very small amount of earth to be displaced or sheared off, as the case may be, so that the force required for rotation is only slightly increased compared to an ungrooved probe.

Since the collar 51 is fixedly connected to the tubular jacket 9 in the embodiment according to FIG. 17, it remains in place thereon when the tubular jacket is used as transport receptacle, the head end opening of the collar 51 and the foot segment 41 of the jacket 9 being closable with closure caps.

In place of the impact pad 36, the collar 51 or the head end 22 of the tubular jacket 9 may be fitted with an adapter (not shown) for connection of a delivery line, for example a hose, through which the sample bodies 7 can be continuously supplied to an adjoining further processing stage or analytical operation. Advantageously, in this case the soil sampling device is used in combination with an hydraulic "handling" unit, known per se, as in FIG. 1.

Advantageously, the tubular jacket 9 is made in a length of about 900 mm, so that with a conventional sample depth of 30 cm, a sufficiently large distance of the impact head 30 from the ground surface is maintained, to facilitate driving in and extracting the manual boring rod 1.

Various modifications in structure and/or function may be made by one skilled in the art to the disclosed embodiments without departing from the scope of the invention as determined by the claims.

We claim:

1. A soil sample probe having a tubular jacket forming a passage including a receiving space for the soil sample;
    a tip releasably attached to one end of the jacket, the tip having a radial shoulder narrowing the passage; and
    non-return means for assisting in the retention of the soil sample, the non-return means comprising a plurality of spring wires distributed on a surface of an annular member disposed substantially axially within the passage, the spring wires being bent toward the axis of the annular member.

2. Device for taking soil a sample comprising:
    a probe having a cylindrical tubular jacket with an upper end including a manipulating means for driving the probe into the soil, the jacket forming a receiving space for accepting the soil sample, the space extending away from the upper end and downward into a cylindrical passage;
    a tip releasably attached to the jacket, the tip having a radial shoulder which narrows the downward passage, the shoulder having at least a peripheral edge with a transition radius which is nearer to the centerline of the jacket; and
    non-return means arranged above the shoulder and protruding into the receiving space, the non-return means comprising at least two spring wires projecting into the receiving space.

3. Device according to claim 2 wherein the transition radius of the peripheral edge is 2 mm.

4. Device according to claims 2 or 3 wherein the tip comprises a head having a periphery in the shape of a truncated cone with a vertex angle of approximately 24°, which periphery terminates at an aperture having a cutting edge with a cutting edge angle of between 30° and 45°, the edge being formed by chamfering the tip head.

5. Device according to claim 4 wherein the cutting edge is set at a predetermined angle to the centerline of the probe.

6. Device according to claims 2 or 3 wherein the spring wires are fixed in the head of the tip.

7. Device according to claims 2 or 3 wherein the upper end of the tubular jacket is pivotably connected to the manipulating means by a linking cuff for closing the upper end of the jacket.

8. Device according to claim 7 wherein an upper peripheral edge of a receptacle for receiving a sole sample is supported on a surface of the manipulating means adjacent the linking cuff, and the upper end of the tubular jacket terminates in a recess in the linking cuff, the recess having a larger diameter than the outside diameter of the tubular jacket.

9. Device according to claim 7 wherein the manipulating means has an impact pad for driving the probe into the soil by hand and is swingable relative to the probe into a releasable locked position.

10. Device according to claim 7 wherein the manipulating means is one end of an actuating cylinder, the other capable of being mounted on a mobile unit.

11. Device according to claim 4 wherein the tip has an external thread capable of being screwed into a lower end of the tubular jacket until the tip head makes flush connection therewith, and a segment at least partially projecting radially inwardly of the tubular jacket towards the centerline of the probe, to form a supporting means for a receptacle to receive the soil sample.

12. Device according to claim 11 wherein the tip is capable of being vented by means of at least one groove extending essentially in an axial direction, which groove is formed in a radially enlarged jacket segment of the tip and open towards the upper end and a lower end of the probe.

13. Device according to claim 12 wherein the groove has a cross section substantially in the form of a circular arc and a crest line of the groove lies radially outwardly of the periphery of the tubular jacket.

14. Device according to claim 11 wherein the receptacle for receiving the soil sample is introduceable from the upper end of the tubular jacket and comprises one or more sleeves of rigid shape.

15. Device according to claims 2 or 3 wherein the tip in the region of the transition to the tubular jacket is enlarged radially outward in the shape of a double cone, and the tubular jacket is usable as a receptacle for holding the soil sample.

16. Device according to claim 15 wherein the tip engages a terminal segment of the tubular jacket and is in threaded engagement therewith, the terminal segment of the tubular jacket being capable of being screwed in until it makes flush contact with an abutment shoulder of the tip formed in the passage.

17. Device according to claim 16 wherein the spring wires are fixed in an annular member supported in the passage on the abutment shoulder, the annular member forming an abutment for the terminal segment of the tubular jacket.

18. Device according to claims 2 or 3 wherein the upper end of the tubular jacket is provided with a collar and an impact pad, a peg resting on an end segment of the collar by a radially enlarged shoulder, the peg having a bore in which a cross-bar can be inserted for removing the probe out of the soil.

19. Device according to claims 2 or 3 wherein the tubular jacket has on its outer surface at least two bulges extending in an axial direction and projecting by a predetermined amount from the tubular jacket in more or less semi-circular shape.

20. Device according to claims 2 or 3 wherein a comminution means for preparation of sample bodies, includes a housing for a rotatably mounted powered comminution element, the housing having a funnel-shaped intake at its upper portion, and a lower portion of the housing opens into a mixer container with mixer unit.

21. Device according to claims 2 or 3 wherein the tubular jacket supports at the upper end end a removable impact pad radially traversed by a cross-bar, the tip being releasably attached to the lower end of the jacket and extending radially outwardly of the tubular jacket and having a biconical cross-section, in which at least one axial recess is formed to vent the segments of the sample hole located immediately beneath the tip, the tubular jacket itself being usable as receptacle for holding the sample, and in the region of transition between the tip and the tubular jacket, the receiving space narrows down towards the opening cross-section of the tip by way of the radial shoulder.

22. A tip for a soil sampling probe comprising means forming a receiving space for accepting a soil sample and having an internal passage which is narrowed by a radial shoulder and non-return means disposed within the tip comprising two spring wires, the shoulder having a peripheral edge which extends radially inwardly toward the centerline of the probe.

23. The tip according to claim 22 wherein the spring wires are distributed on a surface of an annular member disposed substantially axially within the passage, the spring wires being bent toward the axis of the annular member.

24. The tip according to claim 22 wherein the non-return means is arranged above the shoulder and the spring wires project into the receiving space.

* * * * *